(12) United States Patent
Monahan et al.

(10) Patent No.: US 8,737,669 B2
(45) Date of Patent: May 27, 2014

(54) EARPIECE PASSIVE NOISE ATTENUATING

(75) Inventors: Michael Monahan, Southborough, MA (US); Ryan C. Silvestri, Franklin, MA (US); Eric M. Wallace, Chelmsford, MA (US); Kevin P. Annunziato, Medway, MA (US)

(73) Assignee: Bose Corporation, Framingham, MA (US)

(*) Notice: Subject to any disclaimer, the term of this patent is extended or adjusted under 35 U.S.C. 154(b) by 132 days.

(21) Appl. No.: 13/193,288

(22) Filed: Jul. 28, 2011

(65) Prior Publication Data
US 2013/0230204 A1    Sep. 5, 2013

(51) Int. Cl.
*H04R 1/10*    (2006.01)

(52) U.S. Cl.
CPC .............. *H04R 1/1016* (2013.01); *H04R 1/105* (2013.01); *H04R 1/1083* (2013.01)
USPC ............ 381/380; 381/325; 381/328; 381/329

(58) Field of Classification Search
CPC .. H04R 25/652; H04R 25/654; H04R 25/656; H04R 2225/021; H04R 2225/023; H04R 2225/025; H04R 1/1016; H04R 1/105; H04R 1/1083
USPC .......... 381/328, 329, 325, 380; 181/130, 135, 181/131
See application file for complete search history.

(56) References Cited

U.S. PATENT DOCUMENTS

| | | | |
|---|---|---|---|
| 588,099 | A | 8/1897 | Blount |
| 931,768 | A | 8/1909 | Kirkpatrick |
| 1,564,474 | A | 12/1925 | Fensky |
| 1,614,987 | A | 1/1927 | Langbeck et al. |
| 1,668,890 | A | 5/1928 | Curran et al. |
| 1,688,910 | A | 10/1928 | Winship |
| 1,753,817 | A | 4/1930 | Aber |
| 1,893,143 | A | 1/1933 | Koch |
| 1,969,559 | A | 8/1934 | Kelly |
| 2,437,490 | A | 3/1948 | Watson |
| 2,521,414 | A | 9/1950 | Schier |
| 2,538,339 | A | 1/1951 | Thomas |
| 2,545,731 | A | 3/1951 | French |
| 2,763,334 | A | 9/1956 | Starkey |
| 2,908,343 | A | 10/1959 | Hummert |

(Continued)

FOREIGN PATENT DOCUMENTS

| | | |
|---|---|---|
| DE | 29718483 U1 | 2/1999 |
| DE | 202011002165 U1 | 5/2011 |

(Continued)

OTHER PUBLICATIONS

International Search Report and Written Opinion dated Oct. 27, 2011 for International application No. PCT/US2011/048233.

(Continued)

*Primary Examiner* — Curtis Kuntz
*Assistant Examiner* — Joshua A Kaufman

(57) ABSTRACT

An earpiece with structure for positioning and retaining the earpiece and with structure for sealing against the entrance to the ear canal to provide passive noise attenuation. The positioning and retaining structure engages features of the lateral surface of the ear. The structure for sealing against the entrance to the ear canal includes a conical structure.

17 Claims, 6 Drawing Sheets

(56) References Cited

U.S. PATENT DOCUMENTS

| | | |
|---|---|---|
| 3,053,061 A | 9/1962 | French |
| 3,157,245 A | 11/1964 | Bernstein |
| D221,442 S | 8/1971 | Feingold |
| 4,010,820 A | 3/1977 | Johnson |
| 4,055,233 A | 10/1977 | Huntress |
| 4,219,018 A | 8/1980 | Draper, Jr. |
| D266,590 S | 10/1982 | Bennett |
| 4,353,364 A | 10/1982 | Woods |
| D274,814 S | 7/1984 | Tang |
| 4,540,063 A | 9/1985 | Ochi et al. |
| 4,646,872 A | 3/1987 | Kamon et al. |
| 4,896,679 A | 1/1990 | St. Pierre |
| D316,550 S | 4/1991 | Sogabe |
| D318,670 S | 7/1991 | Taniguchi |
| 5,048,090 A | 9/1991 | Geers |
| 5,055,233 A | 10/1991 | Borland et al. |
| D326,655 S | 6/1992 | Iribe |
| 5,222,151 A | 6/1993 | Nagayoshi et al. |
| 5,548,643 A | 8/1996 | Dalgleish et al. |
| 5,625,171 A | 4/1997 | Marshall |
| 5,654,530 A | 8/1997 | Sauer et al. |
| 5,668,354 A | 9/1997 | Falco |
| D388,093 S | 12/1997 | Frengley |
| 5,712,453 A | 1/1998 | Bungardt et al. |
| 5,727,566 A | 3/1998 | Leight |
| 5,957,136 A | 9/1999 | Magidson et al. |
| D430,139 S | 8/2000 | Peters et al. |
| D430,547 S | 9/2000 | Yoon |
| D430,860 S | 9/2000 | Yoon |
| 6,129,175 A | 10/2000 | Tutor et al. |
| 6,241,041 B1 | 6/2001 | Leight |
| 6,449,374 B1 | 9/2002 | Skulley et al. |
| D469,755 S | 2/2003 | Hlas et al. |
| D470,122 S | 2/2003 | Hlas et al. |
| D470,123 S | 2/2003 | Hlas et al. |
| D470,128 S | 2/2003 | Hlas et al. |
| D470,129 S | 2/2003 | Hlas et al. |
| D471,537 S | 3/2003 | Ham |
| D471,890 S | 3/2003 | Clarkson |
| D473,204 S | 4/2003 | Tanio |
| D478,991 S | 8/2003 | Dyer et al. |
| 6,690,807 B1 | 2/2004 | Meyer |
| 6,795,718 B2 | 9/2004 | Bae |
| 6,819,762 B2 | 11/2004 | Jones et al. |
| 6,820,717 B2 | 11/2004 | Fleming et al. |
| 6,868,284 B2 | 3/2005 | Bae |
| 6,879,697 B2 | 4/2005 | Tøpholm |
| D505,132 S | 5/2005 | Linville et al. |
| 6,944,307 B2 | 9/2005 | Berg |
| D510,574 S | 10/2005 | Okada |
| 6,961,440 B1 | 11/2005 | Schlaegel |
| 7,050,599 B2 | 5/2006 | Baskerville |
| 7,068,803 B2 | 6/2006 | Kuhlmann et al. |
| D525,962 S | 8/2006 | Elson |
| D538,271 S | 3/2007 | Kim et al. |
| 7,233,676 B2 | 6/2007 | Bayer |
| D558,735 S | 1/2008 | Carr et al. |
| 7,340,075 B2 | 3/2008 | Bayer |
| D566,099 S | 4/2008 | Komiyama |
| D566,691 S | 4/2008 | Andre et al. |
| D568,302 S | 5/2008 | Oh |
| D569,841 S | 5/2008 | Chung et al. |
| 7,394,910 B2 | 7/2008 | Smith et al. |
| D575,277 S | 8/2008 | Gaarde et al. |
| D575,772 S | 8/2008 | Schultz et al. |
| 7,412,068 B2 | 8/2008 | Bayer |
| D578,507 S | 10/2008 | Ando |
| D578,508 S | 10/2008 | Wang |
| D579,006 S | 10/2008 | Kim et al. |
| D582,389 S | 12/2008 | Bose et al. |
| D582,397 S | 12/2008 | Christopher |
| D582,398 S | 12/2008 | Nam et al. |
| D582,889 S | 12/2008 | Bose et al. |
| D584,284 S | 1/2009 | Carr et al. |
| D584,294 S | 1/2009 | Nam et al. |
| D585,881 S | 2/2009 | Nam et al. |
| D588,099 S | 3/2009 | Yuyama |
| D589,945 S | 4/2009 | Esses |
| 7,536,008 B2 | 5/2009 | Howes et al. |
| D596,164 S | 7/2009 | Henning |
| D601,134 S | 9/2009 | Elabidi et al. |
| D602,476 S | 10/2009 | Lee et al. |
| D605,170 S | 12/2009 | Keinanen |
| D605,628 S | 12/2009 | Ando |
| D607,875 S | 1/2010 | Pedersen, II |
| D618,219 S | 6/2010 | Burgett et al. |
| D618,221 S | 6/2010 | Fahrendorff et al. |
| D620,927 S | 8/2010 | Li |
| D621,817 S | 8/2010 | Brickstad |
| D622,265 S | 8/2010 | Rye |
| D622,704 S | 8/2010 | Fahrendorff et al. |
| 7,778,410 B2 | 8/2010 | Liu et al. |
| D628,188 S | 11/2010 | Koch |
| D633,481 S | 3/2011 | Chen |
| D634,305 S | 3/2011 | Hoggarth |
| 7,949,127 B2 | 5/2011 | Pedersen et al. |
| D640,670 S | 6/2011 | Rye |
| 7,965,855 B1 | 6/2011 | Ham |
| D641,008 S | 7/2011 | Lee et al. |
| D641,747 S | 7/2011 | Gisborne |
| D645,458 S | 9/2011 | Silvestri et al. |
| 8,270,648 B2 * | 9/2012 | Murozaki ............. 381/328 |
| 2002/0096391 A1 | 7/2002 | Smith et al. |
| 2002/0172386 A1 | 11/2002 | Bayer |
| 2003/0091210 A1 | 5/2003 | Baskerville |
| 2004/0045558 A1 | 3/2004 | Taylor et al. |
| 2004/0163653 A1 | 8/2004 | Fleming |
| 2006/0067556 A1 | 3/2006 | Bailey et al. |
| 2006/0177080 A1 | 8/2006 | Smith |
| 2006/0188122 A1 | 8/2006 | Smith |
| 2006/0215864 A1 | 9/2006 | Espersen et al. |
| 2007/0116309 A1 | 5/2007 | Smith |
| 2007/0183615 A1 | 8/2007 | Wurfel |
| 2007/0254725 A1 | 11/2007 | Smith |
| 2008/0085030 A1 | 4/2008 | Smith |
| 2008/0159577 A1 | 7/2008 | Smith |
| 2008/0181441 A1 | 7/2008 | Smith |
| 2008/0247561 A1 | 10/2008 | Smith |
| 2009/0092269 A1 | 4/2009 | Nielsen et al. |
| 2009/0101433 A1 * | 4/2009 | Stiehl et al. ............. 181/129 |
| 2009/0141923 A1 | 6/2009 | Smith |
| 2009/0180654 A1 | 7/2009 | Nielsen |
| 2009/0202094 A1 | 8/2009 | Ammitzboll et al. |
| 2009/0226025 A1 | 9/2009 | Howes et al. |
| 2009/0323993 A1 | 12/2009 | Slemming et al. |
| 2010/0278364 A1 | 11/2010 | Berg |

FOREIGN PATENT DOCUMENTS

| | | |
|---|---|---|
| EP | 368125 A2 | 5/1990 |
| EP | 786241 B1 | 7/1997 |
| EP | 1377113 A2 | 1/2004 |
| EP | 1594340 A1 | 11/2005 |
| JP | 2001333484 A | 11/2001 |
| JP | 2005184579 A | 7/2005 |
| WO | 0150813 A2 | 7/2001 |
| WO | 0150993 A1 | 7/2001 |
| WO | 2004068896 A2 | 8/2004 |
| WO | 2006104981 A2 | 10/2006 |
| WO | 2009030229 A1 | 3/2009 |
| WO | 2010-031775 A1 | 3/2010 |
| WO | 2010-040350 A1 | 4/2010 |
| WO | 2010040351 A1 | 4/2010 |

OTHER PUBLICATIONS

International Search Report and the Written Opinion of the International Searching Authority for PCT/US2012/047975 dated Mar. 18, 2013.

* cited by examiner

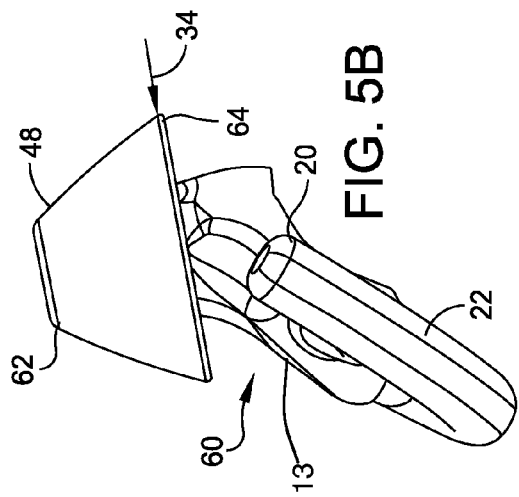
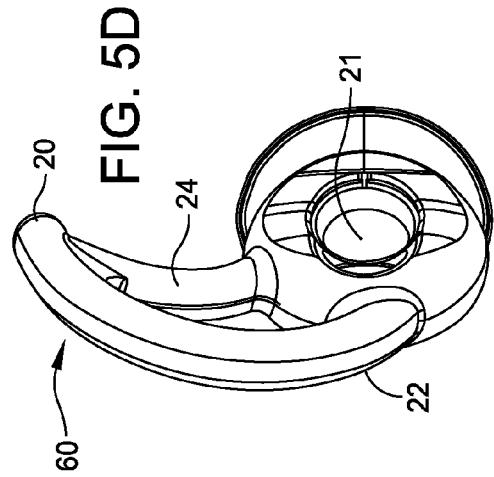
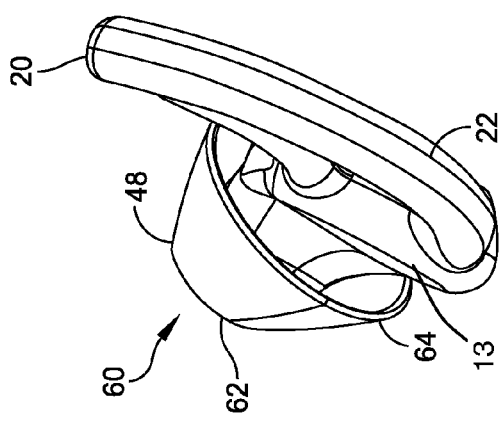
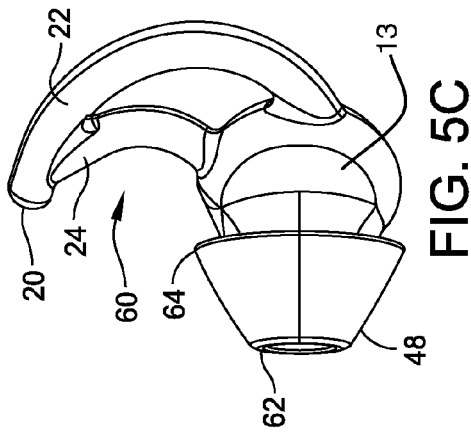
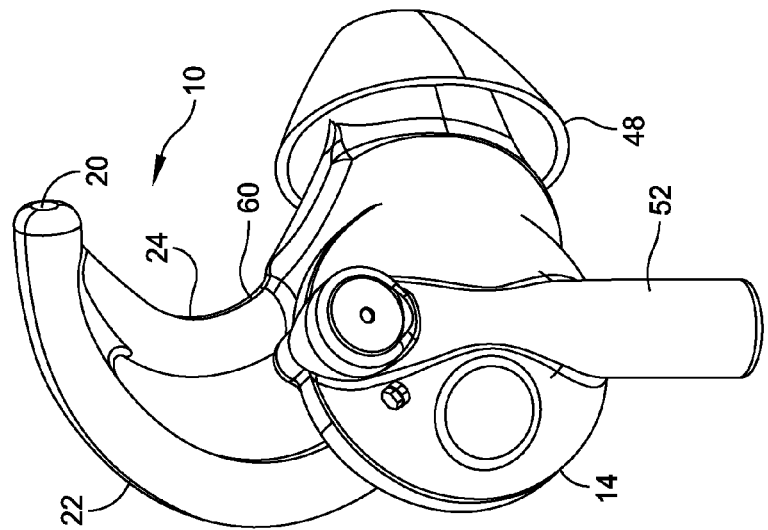

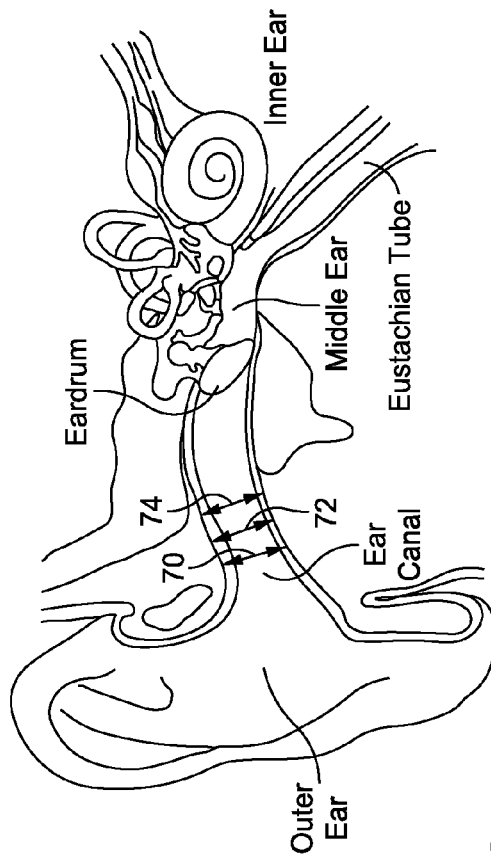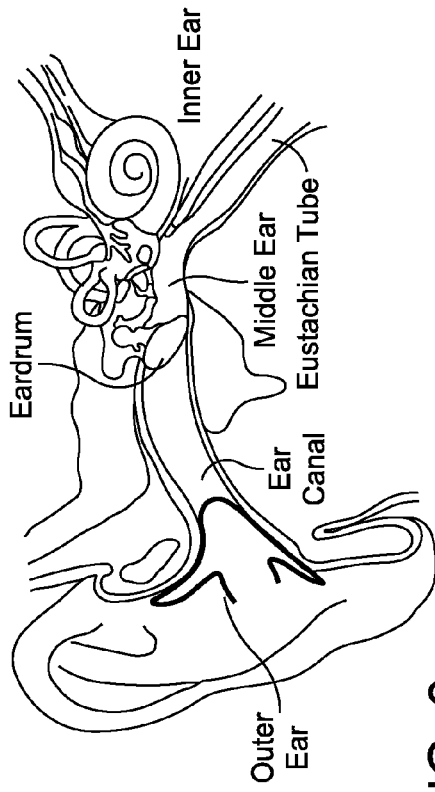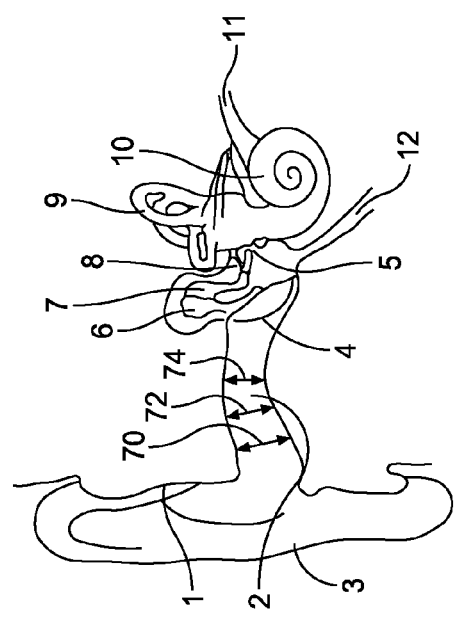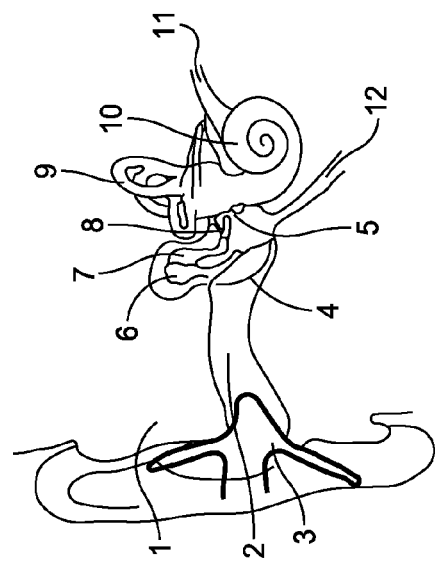
FIG. 4
FIG. 6

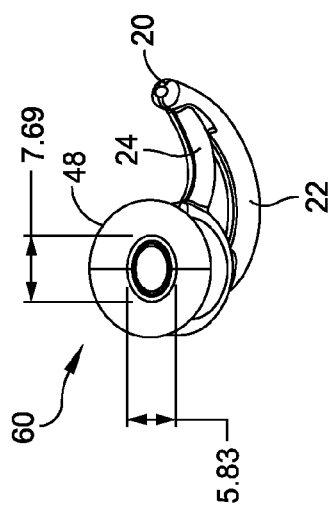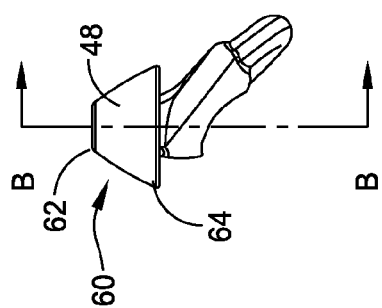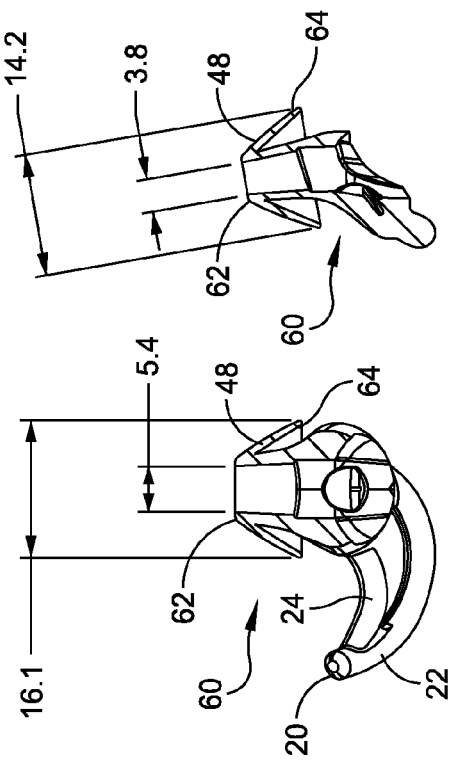

EARPIECE PASSIVE NOISE ATTENUATING

BACKGROUND

This specification describes a structure for providing passive noise attenuation by an in-ear earpiece and for positioning and retaining the earpiece in the ear.

SUMMARY

In one aspect, an in-ear earpiece includes an acoustic driver; an acoustic passage to conduct sound waves radiated by the acoustic driver to an ear canal of a user; a positioning and retaining structure to engage features of the lateral surface of an ear of the user to position the earpiece and to hold the earpiece in place without any structure external to the earpiece; and a substantially conical structure configured so that the smaller end of the conical structure is smaller than the entrance to an ear canal of a user and so that the larger end of the conical structure is larger than the entrance to the ear canal of the user, formed of material that conforms to the entrance to the ear canal to seal the ear canal. The material may have a hardness of 30 Shore A or less. The material may have a modulus of 2 gf/mm or less. The material may be silicone rubber. The material may be a thermoplastic elastomer. The material may be a thermoplastic polyurethane. The positioning and retaining structure may include a first leg and a second leg attached to each other at an attachment end to form a tip and attached to a body of the earpiece at the other end. The positioning and retaining structure may provide at least three modes for preventing clockwise rotation of the earpiece past a rotational position. The modes may include an extremity of the tip contacting the base of the helix; the extremity of the tip becoming wedged under the anti-helix in the cymba concha region; and the inner leg contacting the base of the helix. The positioning and retaining structure may include an inner leg and an outer leg. The inner leg and the outer leg may be attached at an attachment end to the body and attached at a joined end to each other. With the earpiece in its intended position, the outer leg may be urged against the anti-helix at the rear of the concha, the body engages the ear canal; and at least one of the tip is under the anti-helix; or a portion of at least one of the body and the outer leg are under the anti-tragus. The positioning and retaining structure may include an inner leg and an outer leg attached at attachment end to each other and at a second end to an earpiece body. The inner leg and outer leg may be arranged to provide at least three modes for preventing clockwise rotation of the earpieces. The modes may include the tip contacts the base of the helix; the tip becomes wedged under the anti-helix; and the inner leg contacts the base of the helix. The inner leg and the outer leg may be further arranged so that with the earpiece in its intended position, the outer leg is urged against the anti-helix at the rear of the concha, the body engages the ear canal; and at least one of the tip is under the anti-helix; or a portion of at least one of the body and the outer leg are under the anti-tragus. The substantially conical structure may include an opening therethrough to conduct sound waves from the acoustic driver to the ear canal. The opening may be substantially elliptical in cross-section. The substantially conical structure may taper substantially linearly from the large end to the small end. The substantially conical structure may have a substantially uniform thickness. The material of the positioning and retaining structure of the user may have a different hardness than the substantially conical structure. The material of the structure to conduct sound waves radiated by the acoustic driver to an ear canal of a user may have a different hardness than the material of the positioning and retaining structure of the user and than the material of the substantially conical structure.

In another aspect, an eartip for an in-ear earpiece includes positioning and retaining structure to engage features of the lateral surface of an ear to position the earpiece and to hold the earpiece in place without any structure external to the earpiece and a substantially conical structure configured so that the smaller end of the conical structure is smaller than the entrance to an ear canal of a user and so that the larger end of the conical structure is larger than the entrance to the ear canal of the user, formed of material that conforms to the entrance to the ear canal to seal the ear canal. The positioning and retaining structure and the substantially conical structure may include the same material. The positioning and retaining structure and the substantially conical structure may be a unitary structure.

Other features, objects, and advantages will become apparent from the following detailed description, when read in connection with the following drawing, in which:

BRIEF DESCRIPTION OF THE SEVERAL VIEWS OF THE DRAWING

FIG. 2 is an isometric view of an earpiece;
FIG. 4 shows cross-sections of two exemplary human ears;
FIGS. 5A-5D are views of an earpiece;
FIG. 6 shows cross-sections of two exemplary human ears;
FIGS. 7A-7C are views of a portion of the earpiece of FIGS. 2 and 5A-5D;
and
FIGS. 8A and 8B are cross-sections of the earpiece portions of FIGS. 7A-7C.

DETAILED DESCRIPTION

This specification describes an in-ear earpiece that is designed to fit in the right ear. An earpiece that is designed to fit in the left ear is a minor image of the earpiece described below, and operates according to the same principles, and is not described herein.

Figure 1A:
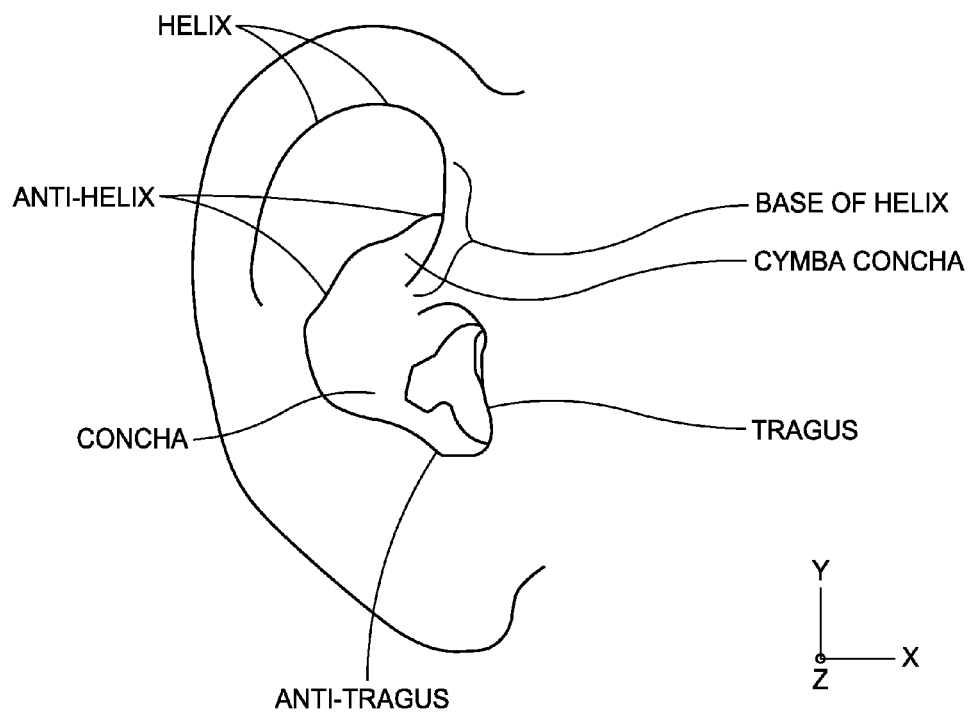
FIG. 1A is a view of the lateral surface of the human ear.
Figure 1B:
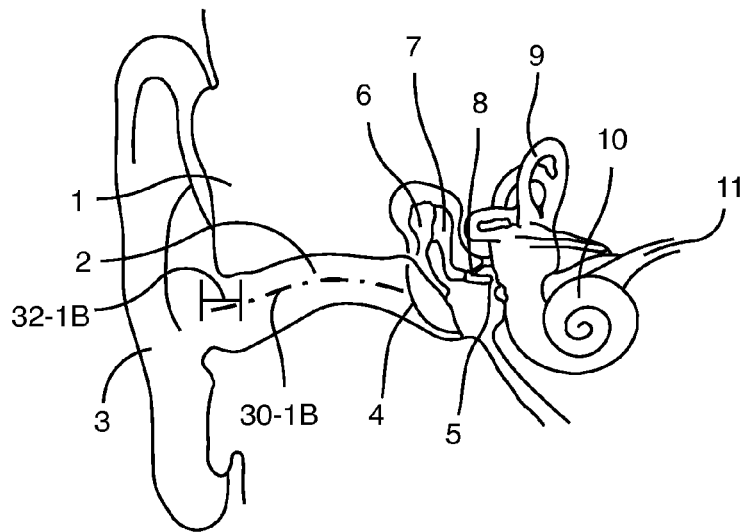
FIGS. 1B and 1C are exemplary cross-sections of the human ear.
Figure 1C:
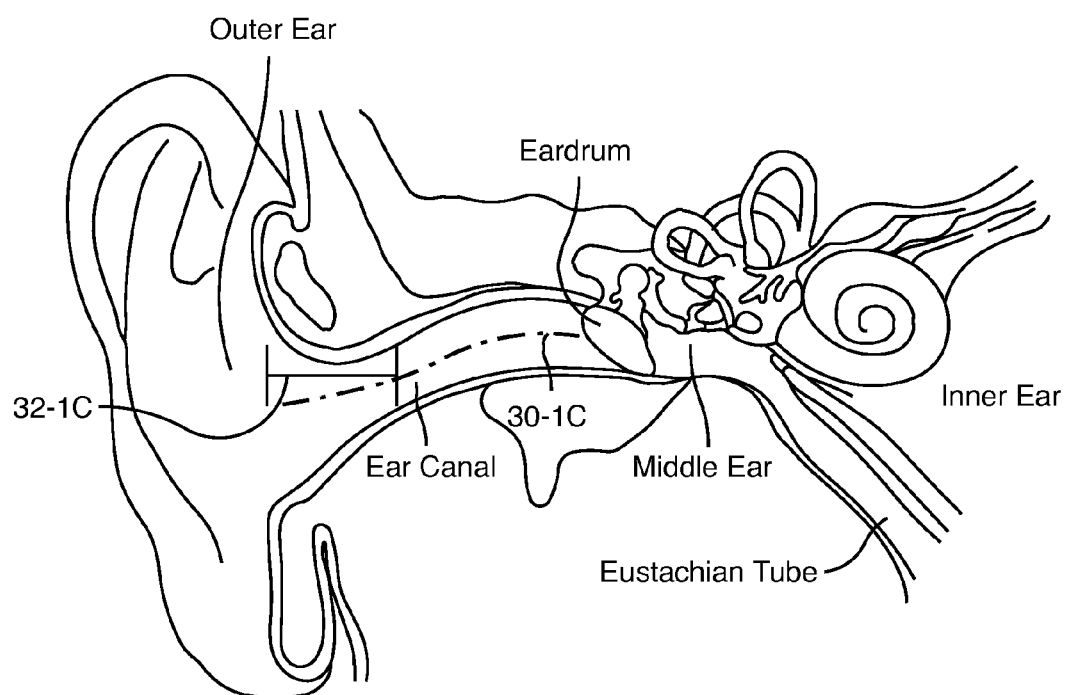

FIG. 1A shows the lateral surface of a human right ear, with some features identified. There are many different ear sizes and geometries. Some ears have additional features that are not shown in FIG. 1A. Some ears lack some of the features that are shown in FIG. 1A. Some features may be more or less prominent than are shown in FIG. 1A. FIGS. 1B and 1C show two exemplary cross-sections of the human ear, with some features identified. The ear canal is an irregularly shaped cylinder with a variable cross sectional area and a centerline that is not straight. Among the features identified is the entrance to the ear canal and the main portion of the ear canal. In this specification the entrance to the ear canal refers to the portion of the ear canal near the concha where the walls of the ear canal are substantially non parallel to the centerline of the ear canal. The precise structure of the human ear varies widely from individual to individual. For example, in the cross section of FIG. 1B, there is a relatively sharp transition from ear canal walls that are non-parallel to a centerline 30-1B of the ear canal to walls that are substantially parallel to a centerline of the ear canal, so the entrance 32-1B to the ear canal in relatively short. In the cross-second of FIG. 1C, there is a more gradual transition from walls that are non-parallel to a centerline of the ear canal to walls that are substantially parallel to a centerline 30-1C of the ear canal, so the entrance 32-1C to the ear canal is relatively long.

FIG. 2 shows an earpiece 10. The earpiece 10 may include a stem 52 for positioning cabling and the like, an acoustic driver module 14, and a tip 60 (more clearly identified in FIGS. 5A-5D). Some earpieces may lack the stem 52 but may include electronics modules (not shown) for wireless communicating with external devices. Other earpieces may lack the stem and the acoustic driver module and may function as passive earplugs. The tip 60 includes a positioning and retaining structure 20, which in this example includes an outer leg 22 and an inner leg 24. The tip also includes a sealing structure 48.

In operation, the earpiece 10 is placed in the ear and is oriented and held in place by positioning and retaining structure 20 and other portions of the earpiece. The tip 60 includes a body 12 which in turn includes a passageway 18 to conduct sound waves radiated by an acoustic driver in the acoustic driver module 14 to the ear canal. The body 12 has a substantially planar surface 13 that substantially rests against the concha at one end. Extending from the tip 60 is the positioning and retaining structure 20 that holds the earpiece in position, without significant contribution from the portions of the eartip that engage the ear canal and without any structure external to the eartip. The positioning and retaining structure 20 includes at least an outer leg 22 and an inner leg 24 that are joined to other portions of the eartip at one end and are joined to each other at the other end. The outer leg is curved to generally follow the curve of the anti helix and/or the cymba concha at the rear of the concha. In general, the compliance/stiffness of the entire positioning and retaining structure is more important than the compliance/stiffness of the material from which the positioning and retaining structure is made or the compliance/stiffness of the any one component of the positioning and retaining structure. The outer leg 22 and inner leg 24 may lie in a plane.

Figure 3:
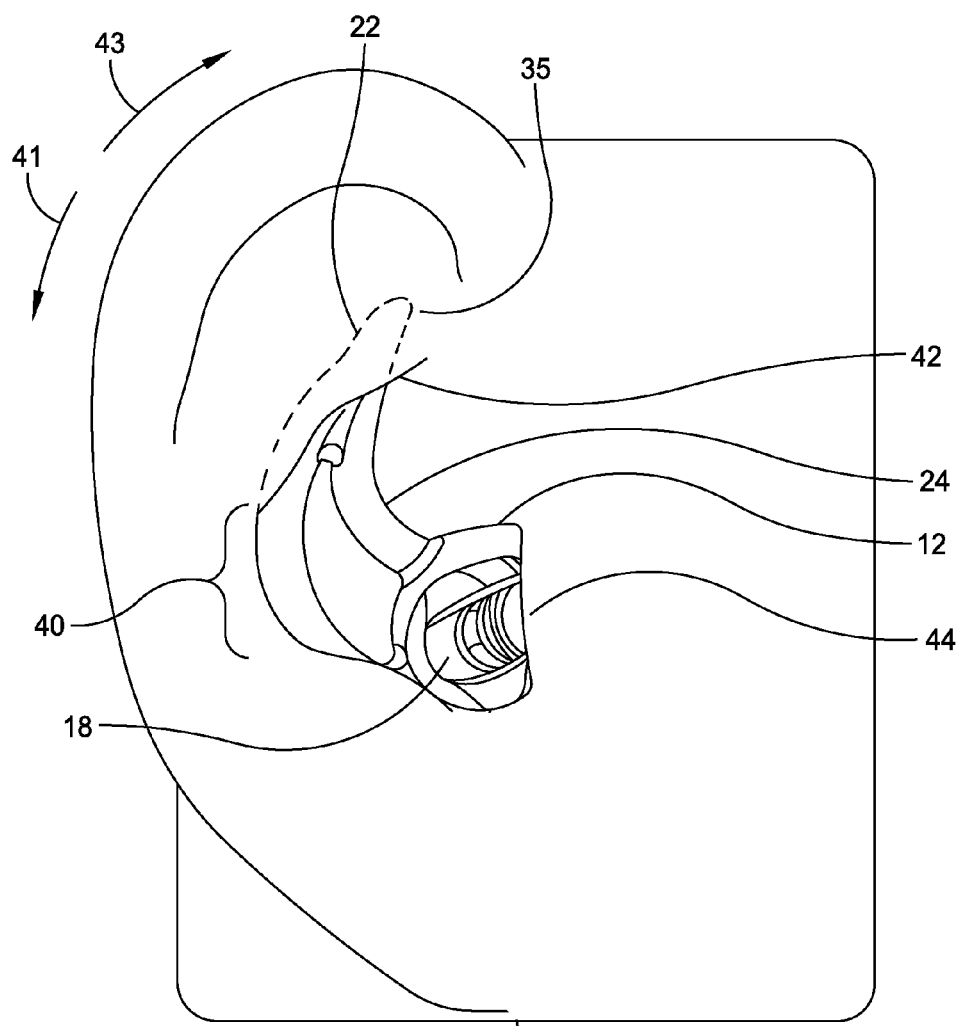
FIG. 3 is a lateral view of an earpiece and a human ear.

Referring now to FIG. 3, the earpiece tip is placed in the ear and pushed gently inward and preferably rotated counter-clockwise as indicated by arrow 41. Pushing the body into the ear causes the outer leg 22 to seat in position underneath the anti-helix, and causes the outlet section of the tip 48 (for convenience, not shown in this view) to enter the ear canal by a small amount, depending on the dimensions and geometry of the entrance to the ear canal.

The body is then rotated clockwise as indicated by arrow 43 until a condition occurs so that the body cannot be further rotated. The conditions could include: the extremity 35 of the tip may contact the base of the helix; inner leg 24 may contact the base of the helix; or the extremity 35 may become wedged behind the anti-helix in the cymba concha region. Though the positioning and retaining structure provides all three conditions (hereinafter referred to as "modes)", not all three conditions will happen for all users, but at least one of the modes will occur for most users. Which condition(s) occur(s) is dependent on the size and geometry of the user's ears.

Rotating the earpiece clockwise also causes the extremity and outer leg to engage the cymba concha region and seat beneath the anti-helix. When the body and positioning and retaining structure 20 are in place, the positioning and retaining structure and/or body contact the ear of most people in at least two, and in many people more, of several ways: a length 40 of the outer leg 22 contacts the anti-helix at the rear of the concha; the extremity 35 of the positioning and retaining structure 20 is underneath the anti-helix; portions of the outer leg 22 or tip 60 (of previous figures) or both are underneath the anti-tragus; and the tip 60 contacts at the entrance to the ear canal under the tragus. The two or more points of contact hold the earpiece in position, providing greater stability. The distributing of the force, and the compliance of the portions of the body and the outer leg that contact the ear lessens pressure on the ear, providing a more comfortable fit.

It is desirable to place the earpiece in the ear so that it is oriented properly, so that it is stable (that is, stays in the ear), so that it is comfortable, and, for some applications so that it provides significant passive attenuation of ambient noise. One way of providing stability and proper orientation is described above and is described more completely in U.S. patent application Ser. No. 12/860,531, now U.S. Pat. No. 8,249,287, incorporated herein by reference in its entirety.

One apparatus for providing significant passive attenuation is a structure (for example a "Christmas tree" structure, as described in U.S. Pat. App. 2004/0163653, a "mushroom" structure, as described by U.S. Pat. No. 5,957,136, or disk shaped flanges, such as described in U.S. Pat. No. 6,129,175, or similar structures) that fit in the main portion of the ear canal and seals to the ear canal itself by exerting radial pressure on the walls of the main portion of the ear canal, as indicated by arrows 70, 72, and 74 of FIG. 4. The radial pressure may result from, or be supplemented by, inward clamping pressure. This apparatus may have some undesirable side effects, such as poor sealing, discomfort, or even pain, because the geometry and size of ear canals vary widely from individual to individual and because the apparatus may intrude farther into the ear canal than desired in some individuals. The main portion of the ear canal, particularly close to the middle ear, is very sensitive, so the farther the structure extends into the ear, the more uncomfortable it is likely to be. Another apparatus for providing significant passive attenuation is structure, apart from the earpiece itself, that provides inward clamping pressure that urges a conformable structure against the side of the head or the side of the ear. Examples include headbands of conventional headphones and yokes of stethoscopes, for example as described in U.S. Pat. No. 4,055, 233. However, for in-the-ear earpieces, light weight and small size are desirable features, and headbands and yokes add weight and structure.

The earpiece of FIG. 2 includes a tip that provides orientation, stability, and good sealing to the entrance to the ear canal and to ear structure outside the ear canal, without excessive radial pressure, and without inward clamping pressure provided by a source not included in the earpiece.

FIGS. 5A-5D shows several views of the tip 60. Not all elements of the tip 60 are identified in all of the views. The tip 60 includes positioning and retaining structure 20, a passageway 21, and sealing structure 48. The sealing structure 48 comprises a frusto-conical structure. The frusto-conical structure may have an elliptical or oval cross section (as viewed in FIG. 7A below), with walls that taper (as viewed in FIGS. 7B, 8A and 8B below) substantially linearly. In one implementation, the structure of the sealing structure and the material from which it is made cause the modulus, when measured in the direction of the arrow 34 of FIG. 5B is in the range of 0.2 to 2 gf/mm. Examples of appropriate materials include silicones, TPUs (thermoplastic polyurethanes) and TPEs (thermoplastic elastomers).

The smaller end 62 of the tip is dimensioned so that it fits inside the ear canal of most users by a small amount and so that the sealing structure 48 contacts the entrance to the ear canal but does not contact the inside of the ear canal. The larger end 64 of the tip is dimensioned so that it is larger than the entrance to the ear canal of most users.

The positioning and retaining structure 20 and the sealing structure 48 may be a single piece, made of the same material, for example a very soft silicone rubber, with a hardness of 30

Shore A or less. The walls of the sealing structure 48 may be of a uniform thickness which may be very thin, for example, less than one mm at the thickest part of the wall and may taper to the base of the frusto-conical structure so that the walls deflect easily, thereby conforming easily to the contours of the ear and providing a good seal and good passive attenuation without exerting significant radial pressure on the ear canal. Since the different parts of the earpiece serve different functions, it may be desirable for different portions of the earpiece to be made of different materials, or materials with different hardnesses or moduli. For example, hardness (durometer) of the retaining structure 20 may be selected for comfort (for example 12 Shore A), the hardness of the tip 48 may be slightly higher (for example 20 Shore A) for better fit and seal, and the hardness of the part of the eartip that mechanically couples the eartip to the acoustic module 14 may be higher (for example 70 Shore A) for better retention and seal to the part of the eartip that mechanically couples the eartip to the acoustic module 14 and in some instances so that the passage through which sound waves travel has a more consistent shape and dimensions.

An eartip according to FIGS. 5A-5D seals to the entrance of the ear canal to provide passive attenuation and exerts little radial pressure against the main portion of the ear canal, or does not contact the main portion of the ear canal at all, as shown in FIG. 6

FIGS. 7A-7C show external views and FIGS. 8A and 8B show cross-sectional views, of the tip 60, with dimensions from a typical embodiment. In the implementations of FIGS. 7A-7C and 8A and 8B, the sealing structure 48 is elliptical, with a major axis of 7.69 mm and a minor axis of 5.83 mm at the smaller end, and a major axis of 16.1 mm and a minor axis of 14.2 mm at the larger end. A sealing structure with these dimensions fits into the ear canal of many users so that the smaller end protrudes into the ear canal by a small amount and does not contact the walls of the ear canal, so that the larger end does not fit in the ear canal, and so that the sealing structure 48 engages the entrance to the ear canal. Smaller or larger versions may be used for users with below- or above-averaged-sized ear, including children. Versions with similar overall size but different aspect ratios between major and minor axes may be provided for users with ear canal entrances that are more- or less-circular than average.

Numerous uses of and departures from the specific apparatus and techniques disclosed herein may be made without departing from the inventive concepts. Consequently, the invention is to be construed as embracing each and every novel feature and novel combination of features disclosed herein and limited only by the spirit and scope of the appended claims.

What is claimed is:

1. An in-ear earpiece comprising:
   an acoustic driver; and
   an eartip comprising, in a unitary structure:
      a cushion body shaped to rest in the concha of a user's ear to support the acoustic driver when the earpiece is positioned in the user's ear;
      an acoustic passage through the cushion body to conduct sound waves radiated by the acoustic driver to an ear canal of the user;
      a nozzle extending the acoustic passage from the cushion body and having an end near the entrance of the ear canal;
      a positioning and retaining structure to engage features of the lateral surface of the ear of the user to position the earpiece and to hold the earpiece in place without any structure external to the earpiece; and
      a substantially conical structure surrounding the nozzle and configured so that the smaller end of the conical structure is smaller than the entrance to the ear canal of the user and so that the larger end of the conical structure is larger than the entrance to the ear canal of the user,
      the conical structure comprising a thin, cone-shaped wall extending from the smaller end at the end of the nozzle to the larger end and open inside, separated from the nozzle, and formed of material that conforms to the entrance to the ear canal to seal the ear canal at an area of transition between the concha and ear canal, without contacting the inside of the ear canal beyond the area of transition;
   wherein the acoustic passage comprises a straight-line passage from the acoustic driver, through the cushion body and the nozzle, and aligned with the entrance of the ear canal, and
   the cushion body rests against the concha and prevents the nozzle and conical structure from being pressed into the ear canal beyond the entrance.

2. The in-ear earpiece of claim 1, wherein the material of the conical structure has a hardness of 30 Shore A or less.

3. The in-ear earpiece of claim 1, wherein the material of the conical structure has a stiffness of 2 gf/mm or less.

4. The in-ear earpiece of claim 1, wherein the material of the conical structure is silicone rubber.

5. The in-ear earpiece of claim 1, wherein the material of the conical structure is a thermoplastic elastomer.

6. The in-ear earpiece of claim 1, wherein the material of the conical structure is a thermoplastic polyurethane.

7. The in-ear earpiece of claim 1, wherein the positioning and retaining structure comprises:
   a first leg and a second leg attached to each other at an attachment end to form a tip and attached to a body of the earpiece at the other end,
   wherein the positioning and retaining structure provides at least three modes for preventing clockwise rotation of the earpiece past a rotational position, the modes including
   an extremity of the tip contacting the base of the helix;
   the extremity of the tip becoming wedged under the anti-helix in the cymba concha region; and
   the inner leg contacting the base of the helix.

8. The in-ear earpiece of claim 1, wherein the positioning and retaining structure comprises:
   an inner leg and an outer leg, the inner leg and the outer leg being attached at an attachment end to the body and attached at a joined end to each other, wherein with the earpiece in its intended position, the outer leg is urged against the anti-helix at the rear of the concha;
   the body engages the ear canal; and
   at least one of
   the tip is under the anti-helix; or
   a portion of at least one of the body and the outer leg are under the anti-tragus.

9. The in-ear earpiece of claim 1, wherein the positioning and retaining structure comprises:
   an inner leg and an outer leg attached at attachment end to each other and at a second end to an earpiece body, the inner leg and outer leg arranged to provide at least three modes for preventing clockwise rotation of the earpieces, the modes including the tip contacts the base of the helix;
   the tip becomes wedged under the anti-helix; and
   the inner leg contacts the base of the helix; the inner leg and the outer leg further arranged so that with the earpiece in its intended position, the outer leg is urged against the anti-helix at the rear of the concha, the body engages the ear canal; and at least one of the tip is under the anti-helix; or a portion of at least one of the body and the outer leg are under the anti-tragus.

10. The in-ear earpiece of claim 1, wherein the acoustic passage comprises in part an opening through the substantially conical structure to conduct sound waves from the acoustic driver to the ear canal.

11. The in-ear earpiece of claim 10, wherein the opening is substantially elliptical in cross-section.

12. The in-ear earpiece of claim 1, wherein the substantially conical structure tapers substantially linearly from the large end to the small end.

13. The in-ear earpiece of claim 1, wherein the substantially conical structure has a substantially uniform thickness.

14. The in-ear earpiece of claim 1, wherein the positioning and retaining structure is composed of a material having a different hardness than the substantially conical structure.

15. The in-ear structure of claim 14, wherein the acoustic passage is bounded by a material having a different hardness than the material of the positioning and retaining structure and than the material of the substantially conical structure.

16. An eartip for an in-ear earpiece having an acoustic driver, comprising, in a unitary structure:

a cushion body shaped to rest in the concha of a user's ear to support the acoustic driver when the earpiece is positioned in the user's ear;

an acoustic passage through the cushion body to conduct sound waves radiated by the acoustic driver to an ear canal of the user;

a nozzle extending the acoustic passage from the cushion body and having an end near the entrance of the ear canal;

a positioning and retaining structure to engage features of the lateral surface of the ear of the user to position the earpiece and to hold the earpiece in place without any structure external to the earpiece; and a substantially conical structure surrounding the nozzle and configured so that the smaller end of the conical structure is smaller than the entrance to the ear canal of the user and so that the larger end of the conical structure is larger than the entrance to the ear canal of the user, the conical structure comprising a thin, cone-shaped wall extending from the smaller end at the end of the nozzle to the larger end and open inside, separated from the nozzle, and formed of material that conforms to the entrance to the ear canal to seal the ear canal at an area of transition between the concha and ear canal, without contacting the inside of the ear canal beyond the area of transition;

wherein the acoustic passage comprises a straight-line passage from the acoustic driver, through the cushion body and the nozzle, and aligned with the entrance of the ear canal, and the cushion body rests against the concha and prevents the nozzle and conical structure from being pressed into the ear canal beyond the entrance.

17. The eartip of claim 16 wherein the positioning and retaining structure and the substantially conical structure comprise the same material.

* * * * *